United States Patent
Pomrink et al.

(10) Patent No.: US 10,143,707 B2
(45) Date of Patent: Dec. 4, 2018

(54) SODIUM CONTAINING SOL-GEL DERIVED BIOACTIVE GLASSES AND USES THEREOF INCLUDING HEMOSTASIS

(71) Applicant: NovaBone Products, LLC, Alachua, FL (US)

(72) Inventors: Gregory J. Pomrink, Newberry, FL (US); Jipin Zhong, Gainesville, FL (US); Zehra Tosun, Gainesville, FL (US); Roy Layne Howell, Gainesville, FL (US); Cecilia Cao, Gainesville, FL (US)

(73) Assignee: NOVABONE PRODUCTS, LLC, Alachua, FL (US)

( * ) Notice: Subject to any disclaimer, the term of this patent is extended or adjusted under 35 U.S.C. 154(b) by 0 days.

(21) Appl. No.: 15/352,009

(22) Filed: Nov. 15, 2016

(65) Prior Publication Data

US 2017/0056445 A1    Mar. 2, 2017

Related U.S. Application Data

(60) Division of application No. 14/312,276, filed on Jun. 23, 2014, now abandoned, which is a continuation-in-part of application No. 14/204,816, filed on Mar. 11, 2014, now Pat. No. 9,498,459.

(60) Provisional application No. 61/782,849, filed on Mar. 14, 2013, provisional application No. 61/786,991, filed on Mar. 15, 2013.

(51) Int. Cl.
| | |
|---|---|
| *A61K 33/42* | (2006.01) |
| *A61K 8/25* | (2006.01) |
| *A61L 27/12* | (2006.01) |
| *C03C 4/00* | (2006.01) |
| *C03C 3/097* | (2006.01) |
| *A61Q 11/00* | (2006.01) |
| *A61L 27/10* | (2006.01) |
| *A61L 27/56* | (2006.01) |
| *A61L 27/54* | (2006.01) |
| *C03B 19/02* | (2006.01) |

(52) U.S. Cl.
CPC ............. *A61K 33/42* (2013.01); *A61K 8/25* (2013.01); *A61L 27/10* (2013.01); *A61L 27/12* (2013.01); *A61L 27/54* (2013.01); *A61L 27/56* (2013.01); *A61Q 11/00* (2013.01); *C03C 3/097* (2013.01); *C03C 4/0007* (2013.01); *A61L 2430/02* (2013.01); *C03B 19/02* (2013.01); *C03C 2204/00* (2013.01)

(58) Field of Classification Search
None
See application file for complete search history.

(56) References Cited

U.S. PATENT DOCUMENTS

| | | |
|---|---|---|
| 5,074,916 A | 12/1991 | Hench et al. |
| 5,558,701 A | 9/1996 | Patel |
| 6,171,986 B1 | 1/2001 | Zhong |
| 6,663,878 B1 | 12/2003 | Greenspan et al. |
| 9,498,459 B2 | 11/2016 | Pomrink et al. |
| 2007/0245772 A1 | 10/2007 | Lieberman et al. |
| 2007/0275021 A1 | 11/2007 | Lee et al. |
| 2009/0186013 A1 | 7/2009 | Stucky et al. |
| 2009/0208428 A1* | 8/2009 | Hill ..................... A61L 27/10 424/52 |
| 2009/0208923 A1 | 8/2009 | Gelfand et al. |
| 2009/0232902 A1 | 9/2009 | Liu et al. |
| 2012/0058250 A1 | 3/2012 | Wu et al. |

FOREIGN PATENT DOCUMENTS

| | | |
|---|---|---|
| WO | WO 2007/144662 A1 | 12/2007 |
| WO | WO 2015/137990 A1 | 5/2015 |

OTHER PUBLICATIONS

Jones, "New trends in bioactive scaffolds: the importance of nanostructure", J Eur Ceramic Soc 29: 1275-1281 (2009).*
Rahaman et al., "Bioactive glass in tissue engineering", Acta Biomaterialia 7: 2355-2373 (2011).*
Adams et al., "Sol-gel synthesis of $SiO_2$—CaO—$Na_2O$—$P_2O_5$ bioactive glass ceramic from sodium metasilicate", New J Glass Ceramics 3:11-15 (2013).*
Ostomel et al., "Spherical Bioactive Glass with enhanced rates of hydroxyapatite deposition and hemostatic activity", Small 2: 1261-1265 (2006).*
Adams et al., "Sol-gel synthesis of $SiO_2$—CaO—$Na_2O$—$P_2O_5$ bioactive glass ceramic from sodium metasilicate", New J Glass Ceramics 3: 11-15 (2013) (Year: 2013).*
Jones, "New trends in bioactive scaffolds: the importance of nanostructure", J Eur Ceramic Soc 29: 1275-1281 (2009) (Year: 2009).*
Ostomel et al., "Spherical Bioactive Glass with enhanced rates of hydroxyapatite deposition and hemostatic activity", Small 2: 1261-1265 (2006) (Year: 2006).*
Rahaman et al., "Bioactive glass in tissue engineering", Acta Biomaterialia 7: 2355-2373 (2011) (Year: 2011).*
International Search Report received in related PCT Application No. PCT/US14/22628 dated Jun. 16, 2014.
Cacciotti, et al., "Sol-gel Derived 45S5 Bioglass: Synthesis, Microstructural Evolution and Thermal Behaviour", *J Mater Sci: Mater Med*, 23:1849-66 (2012).
Chen, et al., "A new sol-gel process for producing $Na_2O$-containing bioactive glass ceramics", *Acta Biomaterialia*, V6(10): 4143-53 (2010).
Chen, et al.,"Fabrication and Characterization of Sol-gel Derived 45S5 Bioglass—Ceramic Scaffolds", *Acta Biomaterialia*, 7: 3636-26 (2011).

(Continued)

Primary Examiner — Thor Nielsen
(74) Attorney, Agent, or Firm — Brinks Gilson & Lione

(57) ABSTRACT

A sol-gel bioactive glass precursor, method for making sol-gel glasses, resultant sol-gel bioactive glasses, and methods of use thereof, which include introducing $Na_2O$ into the glass network during the sol-gel process through the use of Na-ethoxide, NaCl, or sodium silicate rather than sodium nitrate. Medical and industrial uses of such glasses.

22 Claims, No Drawings

(56) References Cited

OTHER PUBLICATIONS

Siqueira, et al., "Gel-derived $SiO_2$—CaO—$Na_2O$—$P_2O_5$ bioactive powders: Synthesis and in vitro bioactivity", *Materials Science and Engineering*, 31(5): 983-91 (2011).

International Search Report received in related PCT Application No. PCT/US14/43638 dated Oct. 15, 2014.

International Preliminary Report and Written Opinion received in related PCT Application No. PCT/US2014/022628 dated Sep. 15, 2014.

International Preliminary Report and Written Opinion received in related PCT Application No. PCT/US2014/043638 dated Sep. 22, 2016.

Carta et al., "Sol-gen synthesis of the P2O5—CaO—Na2O—SiO2 system as a novel bioresorbable glass," *J Mater Chem*, 15:2134-2140 (2005).

El-Ghannam, "Advanced bioceramics composite for bone tissue engineering: design principles and structure-bioactivity relationship," *J Biomed Mater Res,* 69A:490-501 (2004).

European reporting letter dated Jan. 6, 2017, European Search report dated Dec. 8, 2016 and communication dated Jan. 3, 2017 received in European Patent Application No. 14768673.7-1354/2969984.

Adams et al., "Sol-Gel Synthesis of $SiO_2$—CaO—$Na_2O$—$P_2O_5$ Bioactive Glass Ceramic from Sodium Metasilicate," *New Journal of Glass and Ceramics*, 3:11-15 (2013).

Ostomel et al., "Spherical Bioactive Glass with Enhanced Rates of Hydroxyapatite Deposition and Hemostatic Activity," *Bioactive Glasses*, 2(11):1261-1265 (2006).

Reporting letter from Australian associate dated Feb. 1, 2018, and Examination Report No. 1 received in Australian Application No. 2014386243 dated Jan. 25, 2018.

Supplementary European Search Report dated Sep. 25, 2017 and European reporting letter dated Sep. 26, 2017 received in European Patent Application No. 14885246.0-1466/3116836.

* cited by examiner

SODIUM CONTAINING SOL-GEL DERIVED BIOACTIVE GLASSES AND USES THEREOF INCLUDING HEMOSTASIS

RELATED APPLICATIONS

The present patent document is a divisional application of U.S. application Ser. No. 14/312,276, filed Jun. 23, 2014, which is a continuation-in-part application of U.S. application Ser. No. 14/204,816, filed on Mar. 11, 2014, now U.S. Pat. No. 9,498,459, which claims the benefit of the filing date under 35 U.S.C. § 119(e) of Provisional U.S. Patent Application Ser. No. 61/782,849, filed Mar. 14, 2013 and Provisional U.S. Patent Application Ser. No. 61/786,991, filed Mar. 15, 2013, which are hereby incorporated by reference in their entirety.

BACKGROUND

This invention relates generally to novel sol-gel derived bioactive glasses containing sodium and uses thereof.

Sol-gel processes for making, bioactive glass using sol-gel technology are generally known. For example, U.S. Pat. No. 5,074,916 (the "'916 patent"), the subject matter of which is incorporated herein by reference, discloses sol-gel processing techniques used to produce alkali-free bioactive glass compositions based on $SiO_2$, $CaO_2$ and $P_2O_5$. The '916 patent discloses that by varying the $SiO_2$ content a range of hydroxyapatite production rates can be obtained. Also, varying the time of exposure to actual or simulated in vivo solutions permits use of a range of allowable proportions of $SiO_2$. The sol-gel derived compositions disclosed in the '916 patent can be chosen to achieve target values for a thermal expansion coefficient, elastic modulus and volume electrical resistivity. Methods of manufacturing near equilibrium dried sol-gel bioactive glasses are described in U.S. Pat. No. 6,171,986 herein incorporated by reference in its entirety.

The '916 patent explains that one of the advantages of sol-gel derived bioactive glasses over melt derived, is that the use of alkali metal oxides such as $Na_2O$ can be avoided in sol-gel derived bioactive glasses. Such alkali metal oxides serve as a flux or aid in melting or homogenization. The '916 patent points out that the presence of alkali metal oxide ions results in a high pH at the interface between the glass and surrounding fluid or tissue in vivo, and that this can induce inflammation and shut down repair. The '916 patent avoids such issues by using only $SiO_2$, $CaO_2$ and $P_2O_5$ and eliminating the traditional need for sodium or other alkali metal compounds to assist in producing bioactivity.

Patent Application Publication U.S. 2009/0208428 states that the presence of the alkali metals, sodium and potassium, at high concentrations in the bioactive glasses can reduce the usefulness of the bioactive glass in vivo. The preferred sol-gel derived glass disclosed in U.S. 2009/0208428 includes strontium and is alkali-metal free.

Bioglass, melt-derived with code name 45S5, contains 45% $SiO_2$ in weight percent with 24.5% CaO, 24.5% $Na_2O$ and 6% $P_2O_5$, and provides a rapid biological response, or in other words, fast bioactivity, when implanted in living tissue as compared to other bioactive glass formulations.

It has been well recognized that the surface reactivity of Bioglass is attributed to its bioactivity. In the early of 1990s, sol-gel bioactive glasses have been reported with higher specific surface area from their porous structure. Since then, 49S, 58S, 68S, 77S, 86S sol-gel compositions have been reported with corresponding 50%, 60%, 70%, 80% and 90% $SiO_2$ in mole percent, respectively. The specific surface area of all of these compositions is more than 100 times greater than melt-derived 45S5 Bioglass. These compositions typically do not contain $Na_2O$ due to the difficulty in incorporating the $Na_2O$ into the glass network.

Some hemostasis products used worldwide, such as Zeolite and starch powders derived products, owe their hemostatic effect to high specific surface area. It is believed that materials with high surface area adsorb water from the blood rapidly and concentrate clotting proteins and platelets to promote instantaneous clot formation. Sol-gel bioactive glasses possess much higher specific surface area, and should be ideal hemostasis materials in addition to their recognized properties of enhancing bone growth, soft tissue growth and healing as well as oral care in applications such as tooth desensitization, anti-gingivitis and tooth whiting. U.S. Patent Application Publication Nos. 2009/0186013 and 2009/0232902, herein incorporated by reference in their entirety, claim that sol-gel made bioactive silica gel with porous structure and high specific surface area, possessed hemostatic effect. But all of the silica gels reported were made from Si, Ca and P precursors or their inorganic compounds and none of silica gels were reported with a sodium precursor.

A few articles have been published recently on sol-gel derived 45S5 Bioglass containing $Na_2O$. See Q Z Chen, Y Lia, L Y Jina, J M W Quinnc, P A Komesaroffe, "A new sol-gel process for producing Na2O-containing bioactive glass ceramics", Acta Biomaterialia V6(10), 4143-53, 2010; R L Siqueira, O P Edgar and D Zanotto, "Gel-derived SiO2-CaO—Na2O—P2O5 bioactive powders: Synthesis and in vitro bioactivity", Materials Science and Engineering: C V 31(5), 983-91, 2011; Q Z Chen, G A Thouas, "Fabrication and Characterization of Sol-gel Derived 45S5 Bioglass-Ceramic Scaffolds", Acta Biomaterialia, 7, 3636-26, 2011; I Cacciotti, M Lombardi, A Bianco rt al., "Sol-gel Derived 45S5 Bioglass: Synthesis, Microstructural Evolution and Thermal Behaviour", J Mater Sci: Mater Med, 23:1849-66, 2012. All of those works used $NaNO_3$ (sodium nitrate) to introduce $Na_2O$ into the Bioglass system during the sol-gel processing. As explained below, a comparative experiment demonstrated that the precipitation could be seen visually on the gel's surface prepared with sodium nitrate after aging, which could result in possible non-homogenous composition. The exact compositions of the reported sol-gel 45S5 Bioglass materials remain a question since no data has been reported in those published works. Also, all of those articles describe the use of high temperature sintering from 700° C. to 1100° C. to prepare the sol-gel 45S5 glass. The high temperature sintering could enable the preparation of a homogenous composition, however this process could reduce the surface area dramatically to yield a dense 45S5 Bioglass. The authors do not provide any porosity and surface area data in these publications.

SUMMARY

In one aspect, the present invention is directed to a sol-gel bioactive glass precursor including a source of Si, Ca, P, and Na, wherein the sodium source is selected from the group consisting of sodium methoxide, sodium tert-butoxide, sodium hydroxide, sodium oxalate, sodium nitrate, sodium sulfate, sodium thiosulfate, sodium dodecyl sulfate, sodium bicarbonate, soda ash, baking soda, and sodium acetate. The Si source may be selected from the group consisting of tetraethylorthosilicate (TEOS), tetramethylorthosilicate (TMOS), fumed silica, colloidal silica, silica gel, sodium silicate, and silicon tetrachloride. The Ca source may be selected from the group consisting of calcium methoxide, calcium chloride diydrate, calcium hydroxide, calcium oxolate hydrate, and calcium citrate tetrahydrate, calcium sulfate dehydrate, calcium carbonate, calcium acetate hydrate. The P source may be triethylphosphate or sodium hexametaphosphate. The source of Na may be present in an amount to provide for 20-30% by weight of $Na_2O$ in a sol-gel bioactive glass. The source of Si may be present in an amount to provide for 20-30% by weight of $SiO_2$ in a sol-gel bioactive glass. The source of Ca may be present in an amount to provide for 20-30% by weight of CaO in a sol-gel bioactive glass. The source of Ca may be present in an amount to provide for 20-30% by weight of CaO in a sol-gel bioactive glass. The source of phosphate may be triethylphosphate and may be present in an amount to provide for 20-30% by weight of $P_2O_5$ in a sol-gel bioactive glass. The bioactive sol-gel glass may be in a granular form, particulate form, matt form, fiber form, hemostatic sponge form, foam form, paste or putty form, or sphere or bead form, or a combination thereof.

Another embodiments relates to a sol-gel bioactive glass comprising Si, Ca, P, and Na, wherein the sol-gel bioactive glass is derived from a mixture including a sodium source selected from the group consisting of sodium methoxide, sodium tert-butoxide, sodium hydroxide, sodium oxalate, sodium nitrate, sodium sulfate, sodium thiosulfate, sodium dodecyl sulfate, sodium bicarbonate, soda ash, baking soda, and sodium acetate.

Further embodiment relates to a method of making a sol-gel bioactive glass including Si, Ca, P, and Na, the method including mixing a sol-gel bioactive glass precursor including a source of Si, Ca, P, and Na, wherein the sodium source is selected from the group consisting of sodium methoxide, sodium tert-butoxide, sodium hydroxide, sodium oxalate, sodium nitrate, sodium sulfate, sodium thiosulfate, sodium dodecyl sulfate, sodium bicarbonate, soda ash, baking soda, sodium silicate, and sodium acetate; aging the mixture, and drying the mixture to form the sol-gel bioactive glass. In the method, the aging may be conducted at a temperature of 50-80° C. for 40-70 hours. The method may further include the step of sintering at 500-900° C. for 15 to 50 hours.

Yet further embodiment relates to a method for achieving hemostasis in a patient in need of treatment thereof comprising contacting the patient with a sol-gel bioactive glass.

Another embodiment relates to a method of inducing rapid coagulation in a bleeding patient comprising contacting the patient with a sol-gel bioactive glass.

Yet further embodiment relates to a method for achieving hemostasis in a patient in need of treatment thereof comprising contacting the patient with the sol-gel bioactive glass made from the sol-gel bioactive glass precursor including a source of Si, Ca, P, and Na, wherein the sodium source is selected from the group consisting of sodium methoxide, sodium tert-butoxide, sodium hydroxide, sodium oxalate, sodium nitrate, sodium sulfate, sodium thiosulfate, sodium dodecyl sulfate, sodium bicarbonate, soda ash, baking soda, and sodium acetate. In the method, Si, Ca, P, and Na may be present in their oxide form of $SiO_2$, $Ca_2O$, $P_2O_5$, and NaO. The sol-gel bioactive glass may further include one or more of K, Mg, Zn, B, F, or Ag.

Further embodiment relates to a method of making a sol-gel bioactive glass including Si, Ca, P, and Na that includes mixing a sol-gel bioactive glass precursor including a source of Si, Ca, P, and Na, wherein the sodium source is selected from the group consisting of sodium methoxide, sodium tert-butoxide, sodium hydroxide, sodium oxalate, sodium nitrate, sodium sulfate, sodium thiosulfate, sodium dodecyl sulfate, sodium bicarbonate, soda ash, baking soda, and sodium acetate, and drying the mixture at a temperature of 100° C. or lower. The method may further include adding a biologically active molecule.

Yet further embodiment relates to a patient comprising contacting the patient with a sol-gel bioactive glass.

Another embodiment relates to a method of repairing bone in a patient comprising contacting the bone in need of treatment with a sol-gel bioactive glass.

Further embodiment relates to a method for achieving hemostasis or inducing rapid coagulation in a patient in need of treatment thereof comprising contacting the patient with the sol-gel bioactive glass comprising Si, Ca, P, and Na, wherein the sol-gel bioactive glass is derived from a mixture including a sodium source, wherein the sodium source is selected from the group consisting of sodium methoxide, sodium tert-butoxide, sodium hydroxide, sodium oxalate, sodium nitrate, sodium sulfate, sodium thiosulfate, sodium dodecyl sulfate, sodium bicarbonate, soda ash, baking soda, and sodium acetate.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

DETAILED DESCRIPTION OF THE PREFERRED EMBODIMENTS

Unless defined otherwise, all technical and scientific terms used herein have the same meaning as commonly understood by one of ordinary skill in the art to which this invention pertains.

A sol-gel bioactive glass precursor, method for making sol-gel glasses, and resultant sol-gel bioactive glasses are disclosed herein which include introducing $Na_2O$ into the glass network during the sol-gel process through the use of Na-ethoxide or NaCl rather than sodium nitrate. The precursor includes organometallic or inorganic salts of elements such as, for example, Si, Ca, Na, P, Ca, and/or B that are converted to their respective oxides after heat treatment. The resultant gels provide a homogenous material. This gel may be heat treated at relatively low temperature of 100° C. or less to preserve the porous structure with a high specific surface area thereby avoiding a sintering step and providing the possibility of adding biologically active molecules such as disclosed in U.S. Pat. No. 5,830,480, the contents of which is hereby incorporated by reference in its entirety. The sol-gel glasses are optionally sintered at 500-1000° C. or preferably 500-900° C., or more preferably, 550-650° C. Bioactive sol-gels made in accordance with the present invention provide significantly improved hemostatic properties as compared to melt-derived 45S5 Bioglass, and other sol-gel compositions. In addition, bioactive sol-gels made in accordance with the present invention exhibited equivalent or better hemostatic properties as compared to some current commercially available hemostasis products.

In certain embodiments, a sol-gel bioactive glass precursor in accordance with the present invention is a mix of ingredients that provide sources of Si, Ca, and Na to provide a phosphate-free sol-gel derived bioglass.

In certain other embodiments, a sol-gel bioactive glass precursor in accordance with the present invention is a mix of ingredients that provide sources of Si, Ca, P, and Na.

Many organometallic compounds or inorganic salts (other than sodium nitrate) providing a source of Si, Ca, P, or Na can be used. For example, an alkoxysilane such as tetraethoxy silane may be used as a source of silica, calcium methoxide may be used as a source of calcium and triethylphoshpate may be used as a source of phosphorous. Sodium chloride or sodium ethoxide may be used as a source of sodium. Sol-gel bioactive precursors and sol-gels made therefrom may further contain K, Mg, Zn, B, F, Ag, Cu, Fe, Mn, Mo, Sr, and Zn.

Silicon oxide is typically present in amounts of 20-86%, or 30-60%, or 30-45% by weight of the bioactive sol gel glass. Many organosilicon or silicon salts may be used as precursors and may be present in amounts sufficient to yield 0-86% by weight $SiO_2$ in the bioactive glass. Colloidal silica or salycic acid may also be used. Other precursors of silica include sodium organometallics (e.g., tetraethylorthosilicate (TEOS) and tetramethylorthosilicate (TMOS)), fumed silica, colloidal silica, silica gel, sodium silicate, and silicon tetrachloride.

The sol gel bioactive glass may further contain sodium. Many organosodium or inorganic sodium salts may be used as a precursor including but not limited to sodium chloride, sodium ethoxide or sodium silicate. Other precursors of sodium include other sodium organometallics (e.g., sodium methoxide, and sodium tert-butoxide), sodium salts (e.g., sodium hydroxide, and sodium oxalate), sodium nitrates (e.g., sodium nitrate), sodium sulfates (e.g., sodium sulfate, sodium thiosulfate, and sodium dodecyl sulfate), sodium carbonates (e.g., sodium bicarbonate, soda ash, and baking soda) and others, such as sodium silicates and sodium acetate.

Such precursors may be used in an amount sufficient to yield 0-40%, 1-55%, 5-15%, 25-30%, or about 10% by weight $Na_2O$ in the bioactive sol gel glass.

The sol-gel bioactive glass may further comprise potassium. The potassium precursors may include but are not limited to organopotassium compounds or inorganic potassium salts such as potassium nitrate ($KNO_3$), potassium sulphate ($K_2SO_4$) and potassium silicates. It is advantageous to provide a bioactive glass composition in which the potassium content is low. If a potassium precursor is included, it may be present in amounts sufficient to yield 0-8 $K_2O$ in the bioactive glass.

The bioactive glass of the present invention preferably comprises calcium. Calcium precursors include but are not limited to organocalcium compounds or inorganic salts of calcium such as calcium nitrate ($Ca(NO_3)_2$), calcium nitrate tetrahydrate ($CaNo_3.4H_2O$), calcium sulphate ($CaSO_4$), calcium silicates or a source of calcium oxide (Lime). Other precursors of calcium include calcium organometallics (e.g., calcium methoxide), calcium salts (e.g., calcium chloride diydrate, calcium hydroxide, calcium oxolate hydrate, and calcium citrate tetrahydrate), calcium nitrates (e.g., calcium nitrate tetrahydrate), calcium sulfates (e.g., calcium sulfate dehydrate), calcium carbonates (e.g., calcium carbonate) and other precursors, such as calcium acetate hydrate. A source of calcium oxide includes any compound that decomposes to form calcium oxide. Release of $Ca^{2+}$ ions from the surface of the bioactive glass aids the formation of the calcium phosphate-rich layer on the surface of the glass. The provision of calcium ions by the bioactive glass can increase the rate of formation of the calcium phosphate-rich layer. However it should be appreciated that the calcium phosphate-rich layer can form without the provision of calcium ions by the bioactive glass, as body fluid itself contains calcium ions. Thus, for the purposes of this invention, bioactive glasses containing no calcium can be used. The calcium precursor may be present in the precursor in an amount sufficient to yield at least 5%, 0-40%, 10-20%, 20-30% or about 25% CaO in the resultant sol-gel glass.

The bioactive glass of the present invention preferably comprises $P_2O_5$. Phosphate precursors include many organophosphates and inorganic phosphate salts including but not limited to triethylphosphate and/or polyphosphates, such as, e.g. sodium hexametaphosphate. Release of phosphate ions from the surface of the bioactive glass aids in the formation of hydroxycarbonated apatite. While hydroxycarbonated apatite can form without the provision of phosphate ions by the bioactive glass, as body fluid itself contains phosphate ions, the provision of phosphate ions by the bioactive glass increases the rate of formation of hydroxycarbonated apatite. The phosphate precursor may be present in an amount sufficient to yield at 0-80%, 0-50%, 20-70%, 20-30%, 25-30%, or about 25% $P_2O_5$ in the resultant glass.

The sol-gel bioactive glass of the present invention may comprise zinc. Zinc precursors include but are not limited to organozinc compounds or inorganic salts containing zinc such as zinc nitrate ($Zn(NO_3)_2$), zinc sulphate ($ZnSO_4$), and zinc silicates and any such compounds that decompose to form zinc oxide. When present, the zinc precursor should be present in amounts sufficient to yield 0.01-5% ZnO in the glass.

The bioactive glass of the present invention may comprise magnesium. Magnesium precursors include but are not limited to organomagnesium compounds or inorganic magnesium salts such as magnesium nitrate ($Mg(NO_3)_2$), magnesium sulphate ($MgSO_4$), magnesium silicates and any such compounds that decompose to form magnesium oxide. When included the magnesium source should be present in an amount sufficient to yield 0.01 to 5% MgO in the bioactive glass.

The sol-gel bioactive glass of the present invention also includes boron. The boron precursors include but are not limited to organoborate compounds, inorganic borate salts, boric acid, and trimethyl borate. A sufficient amount of boron precursor may be used sufficient to provide $B_2O_3$ in amounts of at least 25%, 30% to 50%, 35-45%, or up to 80% by weight in the glass.

The bioactive glass of the present invention may comprise fluorine. Fluorine precursors include but are not limited to organofluorine compounds or inorganic fluorine salts such as calcium fluoride ($CaF_2$), strontium fluoride ($SrF_2$), magnesium fluoride ($MgF_2$), Sodium fluoride (NaF) or potassium fluoride (KF). Fluoride stimulates osteoblasts, and increases the rate of hydroxycarbonated apatite deposition. When present, an amount of fluorine precursor is used to provide 0-35% or 0.01-5% calcium fluoride.

The bioactive sol-gels may further comprise sources of Cu, Fe, Mn, Mo, or Sr. When present, such sources include organometallic and inorganic salts thereof. Each may be present to provide in 0.01 to 5% or more by weight of the respective oxide in the glass.

Bioactive sol-gels in accordance with the present invention are hemostatic materials that are bioabsorbable, that provide for superior hemostasis, and may be fabricated into a variety of forms suitable for use in controlling bleeding from a variety of wounds, both internal and external. Bioactive sol-gel glasses may be in granular or particulate form, matt or fiber form, a hemostatic sponge, incorporated into a foam, or in the form of a paste or putty. The sol-gel glasses may also be in a form of a sphere or a bead, or a combination of all the forms. Exemplary spherical forms were described in U.S. Provisional Application No. 61/786,991, filed Mar.

15, 2013, content of which is incorporated by reference in its entirety. They may also be formulated into settable and non-settable carriers.

Sol-gel bioactive glass is suitable for use in both surgical applications as well as in field treatment of traumatic injuries. For example, in vascular surgery, bleeding is particularly problematic. In cardiac surgery, the multiple vascular anastomoses and cannulation sites, complicated by coagulopathy induced by extracorporeal bypass, can result in bleeding that can only be controlled by topical hemostats. Rapid and effective hemostasis during spinal surgery, where control of osseous, epidural, and/or subdural bleeding or bleeding from the spinal cord is not amenable to sutures or cautery, can minimize the potential for injury to nerve roots and reduce the procedure time. In liver surgery, for example, live donor liver transplant procedures or removal of cancerous tumors, there is a substantial risk of massive bleeding. An effective hemostatic material can significantly enhance patient outcome in such procedures. Even in those situations where bleeding is not massive, an effective hemostatic material can be desirable, for example, in dental procedures such as tooth extractions, as well as the treatment of abrasions, burns, and the like. In neurosurgery, oozing wounds are common and are difficult to treat.

The bioactive sol-gels may be further combined with a bioactive agent. The bioactive agent comprises one of antibodies, antigens, antibiotics, wound sterilization substances, thrombin, blood clotting factors, conventional chemo- and radiation therapeutic drugs, VEGF, antitumor agents such as angiostatin, endostatin, biological response modifiers, and various combinations thereof. The bioactive sol-gels may also be combined with polymers to provide further structural support. For example, porous bioactive glass hemostatic agents may be prepared by a sol gel process described herein that further uses a block copolymer of ethyleneoxide and propylene oxide.

Other uses for the sol-gel compositions of the present invention include filling bone defects, bone repair/regeneration, limb salvage, drug delivery, repair of osteochondral defects, reparing osseous defects, dental hypersensitivity, tooth whitening, and guided tissue regeneration.

EXAMPLES

Preparation of Sol-Gels

Sol Gel Bioactive glasses were prepared with the compositions set forth in Table 1 and as described in 1-1 through 1-6 below:

TABLE 1

Compositions of Sol-gel Bioactive Glasses

| Sample ID | SiO2 (wt %) | CaO (wt %) | P2O5 (wt %) | Na2O (wt %) |
|---|---|---|---|---|
| 45S5 (melt) | 45 | 24.5 | 6 | 24.5 |
| 45S5 (Sol-gel) | 45 | 24.5 | 6 | 24.5 |
| 58S | 58 | 33 | 9 | 0 |
| 77S | 77 | 14 | 9 | 0 |
| 100S | 100 | 0 | 0 | 0 |

Preparation of 1-1. 100S gel (Comparative—no Na, Ca, or P source): the gel was prepared by mixing D. I. water, HCl, TEOS (Tetraethoxysilane) followed by mixing for 60 minutes to facilitate the completion of hydrolysis reaction. Then, the mixture was transferred into a polypropylene mold for aging at 60° C. for 55 hours. After aging, the gel was transferred into drying vessel for drying to 180° C., then heated at 700° C. in the same procedures as reported in U.S. Pat. No. 5,074,916 (the contents of which are hereby incorporated by reference in its entirety). The heat treated gels were ground to <300 μm powders for analysis and testing.

Preparation of 1-2. 77S gel (Comparative—no Na source): the gel was prepared by mixing D. I. water, HCl, TEOS (Tetraethoxysilane) for 30 minutes, adding TEP (Triethylphosphate) into the solution and mixing for another 20 minutes, then adding $CaNO_3.4H_2O$ (Calcium Nitrate tetrahydrate) while mixing for an additional 60 minutes to complete the dissolution of the Calcium Nitrate. Then, the mixture was transferred into a polypropylene mold for aging at 60° C. for 55 hours. After aging, the gel was transferred into drying vessel for drying to 180° C., and then heated at 700° C. in the same procedures as reported in the U.S. Pat. No. 5,074,916. The heat treated gels were ground to <300 μm powders for analysis and testing.

Preparation of 1-3 (Comparative—no Na source). 58S gel: the gel was prepared by mixing D. I. water, HCl, TEOS (Tetraethoxysilane) for 30 minutes, adding TEP (Triethylphosphate) into the solution and mixing another 20 minutes, then adding CaNO3.4H2O (Calcium Nitrate tetra-hydrate) while mixing for an additional 60 minutes to complete the dissolution of the Calcium Nitrate. Then, the mixture was transferred into a polypropylene mold for aging at 60° C. for 55 hours. After aging, the gel was be transferred into drying vessel for drying to 180° C., and then heated at 700° C. in the same procedures as reported in the U.S. Pat. No. 5,074,916. The heat treated gels were ground to <300 μm powders for analysis and testing.

Preparation of 1-4. 45S5 gel#1 (Includes sodium ethoxide as Na source): the gel was prepared by mixing half the amount of D. I. water, HCl, TEOS (Tetraethoxysilane) for 30 minutes, adding TEP (Triethylphosphate) into the solution and mixing another 20 minutes, then adding the rest of D. I. water, Calcium Methoxide, and Sodium Ethoxide, while mixing for 60 minutes to complete the hydrolysis reaction. Then, the mixture was transferred into a polypropylene mold for aging at 60° C. for 55 hours. After aging, the gel was transferred into drying vessel for drying to 180° C., and then heated at 550° C. in the same procedures as reported in the U.S. Pat. No. 5,074,916. The heat treated gels were ground to <300 μm powders for analysis and testing.

Preparation of 1-5. 45S5 gel#2 (Includes NaCl as Na source): the gel was prepared by mixing D. I. water, HCl, TEOS (Tetraethoxysilane) for 30 minutes, adding TEP(triethylphosphate) into the solution and mixing another 20 minutes, then adding $CaNO_3.4H_2O$ (Calcium Nitrate tetrahydrate) and NaCl while mixing for an additional 60 minutes to complete the dissolution of the Calcium Nitrate and NaCl. Then, the mixture was transferred into a polypropylene mold for aging at 60° C. for 55 hours. After aging, the gel was transferred into drying vessel for drying at 180° C., and then heated to 550° C. using the same procedure as reported in U.S. Pat. No. 5,074,916.

Preparation of 1-6. 45S5 gel#3 (Comparative—includes sodium nitrate as Na source): the gel was prepared by mixing D. I. water, HCl, TEOS (Tetraethoxysilane) for 30 minutes, adding TEP(triethylphosphate) into the solution and mixing another 20 minutes, then adding $CaNO_3.4H_2O$ (Calcium Nitrate tetra-hydrate) and $NaNO_3$ (Sodium Nitrate), while mixing for an additional 60 minutes to complete the dissolution of the Calcium Nitrate and Sodium Nitrate. Then, the mixture was transferred into a polypropylene mold for aging at 60° C. for 55 hours. After aging, the precipitation could be seen visually. After aging, the gel was transferred into drying vessel for drying at 180° C., and then heated to 550° C. using the same procedure as reported in U.S. Pat. No. 5,074,916.

The following porous structure data was obtained from the foregoing compositions:

| Sample ID | Specific Surface Area $m^2$/gram | Pore Size Diameter (Angstroms) |
|---|---|---|
| Standard Specifications | 216 | 203 |
| 45S5(Melt) | 0.1 | 0 |
| 45S5(Sol-gel) | 31 | 98 |
| 58S | 166 | 96 |
| 77S | 414 | 30 |
| 100S | 561 | 40 |

Hemostasis Studies

The male adult Wistar rats were anesthetized by intraperitoneal injection of pentobarbital (40 mg/kg). An abnormal incision was made and the left kidney was isolated. A thin flexible plastic tray was placed under the kidney and the kidney is wrapped with pre-weighted degrease cotton. Heparin sodium (300 IU/kg) was then intravenous injected. Five minutes later, an atraumatic clamp was placed across the renal vascular pedicle, the caudal pole of the kidney was extruded through the ring about 4 mm protruded above the plate and the tissue was severed with a scalpel blade. The hemostatic agent was applied to the cutting surface of the kidney before the clamp was removed. Bleeding time and the amount of blood dropped(Blood Wt) were measured.

Based on the statistic results of this test, the sol-gel 58S demonstrated a comparable hemostatic effect to FloSeal, a commercial available product in the market. The order is, 58S>melt 45S5>Starch. All of the test materials are better than No-treatment control.

4-2. Study #2

The tested samples: 45S5(Melt), 45S5(Sol-gel), 58S, 77S, 100S

Control group: NexStat(Hemostasis, LLC),

Blank Control: No material applied

Each test article was tested in 3 doses: 5 μl, 15 μl and 50 μl, and each dose was conducted 6 tests.

Test Results

TABLE 4

| Blank Control | |
|---|---|
| Bleeding time (s) | Blood Wt Collected (g) |
| 647 ± 25.57 | 5.35 ± 0.17 |

TABLE 5

Bleeding Time and Blood Drop for Study #2 in the Rat Model of Partial Nephrectomy

| | Materials | | | | | | | | | |
|---|---|---|---|---|---|---|---|---|---|---|
| | NexStat | | 45S5(Sol-gel) 1-4 | | 58S | | 77S | | 100S | |
| Dose | Bleeding Time (s) | Blood Wt (g) | Bleeding Time (s) | Blood Wt (g) | Bleeding Time (s) | Blood Wt (g) | Bleeding Time (s) | Blood Wt (g) | Bleeding Time (s) | Blood Wt (g) |
| 5 μl | 341 ± 17.5* | 3.22 ± 0.16* | 220.6 | 1.9 | 552 ± 16.7 | 4.68 ± 0.21 | 466 ± 32.3* | 4.10 ± 0.18 | 587 ± 16.7 | 4.90 ± 0.13 |
| 15 μl | 166 ± 9.7* | 1.65 ± 0.10* | 178 | 1.12 | 396 ± 9.6* | 3.83 ± 0.24 | 240 ± 16.2* | 2.43 ± 0.15* | 450 ± 13.3* | 3.67 ± 0.20* |
| 50 μl | 80 ± 7.2* | 1.00 ± 0.08* | 78 | 0.66 | 216 ± 7.7* | 2.15 ± 0.20* | 92 ± 7.8* | 0.98 ± 0.07* | 286 ± 8.5* | 2.48 ± 0.18* |

4-1. Study #1

The tested samples: 45S5(Melt), Sol-gel 58S

Control group: FloSeal, Starch (both are commercially available products used in the worldwide market)

Blank Control: No material applied

Each test article was tested in 50 mg, and conducted 6 tests.

TABLE 3

Test Results Bleeding Time and Blood Drop for Study #1 in the Rat Model of Partial Nephrectomy

| Group | Number | Bleeding time (Seconds) | Blood dropped (ml) |
|---|---|---|---|
| No-treatment Control | 5 | 624 ± 36 | 4.3 ± 0.4 |
| Edible starch | 5 | 408 ± 24 | 3.0 ± 0.5 |
| Melt-derived 45S5 Bioglass | 5 | 264 ± 24 | 2.1 ± 0.3 |
| Bioglass 58S Gel | 5 | 216 ± 12 | 1.0 ± 0.1 |
| FloSeal | 5 | 186 ± 12 | 1.0 ± 0.1 |

Based on the statistic results of this test, the sol-gel 45S5 demonstrated the best hemostatic effect. The order is, sol-gel 45S5>NexStat>77S>58S>77S>melt 45S5.

Sol-gel 45S5 demonstrated the best hemostatic effect compared with other tested materials, even some commercially available hemostasis products. Sol-gel 45S5, with porous structure, has 30 times higher surface area then melt derived 45S5 Bioglass. The high surface is functions to adsorb water from the blood rapidly and concentrate clotting proteins and platelets to promote instantaneous clot formation. In addition, calcium ions release from the glass function to complex with the carboxylic acid functional groups of the proteins within the site to facilitate clot formation. Although sol-gel 45S5 specific surface area is not the highest compared with other sol-gel materials such as the 58S, 77S and 100S, it can be assumed that the ionic exchange between Na+ inside sol-gel 45S5 and OH− would create a large amount of silanol groups on the sol-gel 45S5 surface or inside pores, which would facilitate the physical and chemical absorption of water onto the surface of the glass.

Due to its fast surface activity, $Ca^{2+}$ release from sol-gel 45S5 would also be very dramatic. As previously described the calcium ions will complex with the surrounding proteins most notably fibrin acting as a type of glue to hold the fibrin monomers to each other to form the polymeric fiber. The resultant fibrin fibers form a loose meshwork, which functions to entrap erythrocytes, thus forming a clot that stops the flow of blood. All of these factors contribute to the hemostatic effect exhibited by the sol-gel 45S5 Bioglass.

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, that are intended to define the spirit and scope of this invention.

The invention claimed is:

1. A method of making a sol-gel bioactive glass comprising:
   mixing a sol-gel bioactive glass precursor including a source of Si, Ca, P, and Na, wherein the source of Na is selected from the group consisting of sodium tert-butoxide, sodium hydroxide, sodium oxalate, sodium sulfate, sodium thiosulfate, sodium dodecyl sulfate, sodium bicarbonate, soda ash, baking soda, sodium silicate, and sodium acetate;
   aging the mixture;
   drying the mixture to form the sol-gel bioactive glass; and
   sintering the sol-gel bioactive glass at 550-650° C. for 15 to 50 hours.

2. The method of claim 1, wherein said aging is conducted at a temperature of 50-80° C. for 40-70 hours.

3. The method of claim 1, wherein the drying step is at a temperature of 100° C. or lower.

4. The method of claim 1, further comprising adding a biologically active molecule.

5. The method of claim 1, wherein the source of Si is selected from the group consisting of tetraethylorthosilicate (TEOS), tetramethylorthosilicate (TMOS), fumed silica, colloidal silica, silica gel, sodium silicate, and silicon tetrachloride.

6. The method of claim 1, wherein the source of Ca is selected from the group consisting of calcium methoxide, calcium chloride dihydrate, calcium hydroxide, calcium oxalate hydrate, calcium citrate tetrahydrate, calcium sulfate dehydrate, calcium carbonate and, calcium acetate hydrate.

7. The method of claim 5, wherein the source of Ca is selected from the group consisting of calcium methoxide, calcium chloride dihydrate, calcium hydroxide, calcium oxalate hydrate, calcium citrate tetrahydrate, calcium sulfate dehydrate, calcium carbonate and, calcium acetate hydrate.

8. The method of claim 1, wherein the source of P is triethylphosphate or sodium hexametaphosphate.

9. The method of claim 1, wherein the source of Na is present in an amount to provide for 20-30% by weight of $Na_2O$ in the sol-gel bioactive glass.

10. The method of claim 1, wherein the source of Si is present in an amount to provide for 20-30% by weight of $SiO_2$ in the sol-gel bioactive glass.

11. The method of claim 1, wherein the source of Ca is present in an amount to provide for 20-30% by weight of CaO in the sol-gel bioactive glass.

12. The method of claim 1, wherein the source of phosphate is triethylphosphate and is present in an amount to provide for 20-30% by weight of $P_2O_5$ in the sol-gel bioactive glass.

13. A sol-gel bioactive glass comprising Si, Ca, P, and Na, produced by the method of claim 1 wherein sintering consists of sintering the sol-gel bioactive glass at 550-650° C. for 15-50 hours.

14. The sol-gel bioactive glass of claim 13, the sol-gel bioactive glass having a porous structure and a significantly higher specific surface area as compared to a melt-derived bioactive glass of the same composition, wherein the sol-gel bioactive glass is strontium free.

15. The sol-gel bioactive glass of claim 13, wherein Si, Ca, P, and Na are present in their oxide form of $SiO_2$, $Ca_2O$, $P_2O_5$, and NaO.

16. The sol-gel bioactive glass of claim 15, further comprising one or more of K, Mg, Zn, B, F, or Ag.

17. The sol-gel bioactive glass of claim 13, wherein the bioactive sol-gel glass is in a granular form, particulate form, matt form, fiber form, hemostatic sponge form, foam form, paste or putty form, or sphere or bead form, or a combination thereof.

18. The sol-gel bioglass of claim 14, wherein the significantly higher specific surface area is at least 30 times higher than the melt-derived bioactive glass specific surface area.

19. A method for achieving hemostasis in a patient in need of treatment thereof comprising contacting the patient with the sol-gel bioactive glass produced by the method of claim 1 wherein sintering consists of sintering the sol-gel bioactive glass at 550-650° C. for 15-50 hours.

20. A method of inducing rapid coagulation in a bleeding patient comprising contacting the patient with the sol-gel bioactive glass produced by the method of claim 1 wherein sintering consists of sintering the sol-gel bioactive glass at 550-650° C. for 15-50 hours.

21. A method of treating wounds in a patient comprising contacting the patient with the sol-gel bioactive glass produced by the method of claim 1 wherein sintering consists of sintering the sol-gel bioactive glass at 550-650° C. for 15-50 hours.

22. A method of repairing bone in a patient comprising contacting the bone in need of treatment with the sol-gel bioactive glass prepared by the method of claim 1 wherein sintering consists of sintering the sol-gel bioactive glass at 550-650° C. for 15-50 hours.

* * * * *